(12) United States Patent
Zhang et al.

(10) Patent No.: US 9,376,679 B2
(45) Date of Patent: Jun. 28, 2016

(54) MICROVESICLES CARRYING SMALL INTERFERING RNAS, PREPARATION METHODS AND USES THEREOF

(75) Inventors: Chenyu Zhang, Beijing (CN); Ke Zeng, Beijing (CN); Danqing Liu, Beijing (CN); Yujing Zhang, Beijing (CN); Hongwei Gu, Beijing (CN)

(73) Assignee: Micromedmark Biotech Co. Ltd., Beijing (CN)

(*) Notice: Subject to any disclaimer, the term of this patent is extended or adjusted under 35 U.S.C. 154(b) by 589 days.

(21) Appl. No.: 13/700,067

(22) PCT Filed: May 26, 2010

(86) PCT No.: PCT/CN2010/073262
§ 371 (c)(1),
(2), (4) Date: Apr. 26, 2013

(87) PCT Pub. No.: WO2011/147086
PCT Pub. Date: Dec. 1, 2011

(65) Prior Publication Data
US 2013/0209544 A1    Aug. 15, 2013
US 2014/0302119 A2    Oct. 9, 2014

(51) Int. Cl.
| | | |
|---|---|---|
| *C12N 15/113* | (2010.01) | |
| *C12N 15/11* | (2006.01) | |
| *A61K 9/127* | (2006.01) | |
| *C12Q 1/68* | (2006.01) | |
| *C12N 15/88* | (2006.01) | |

(52) U.S. Cl.
CPC .............. *C12N 15/113* (2013.01); *A61K 9/127* (2013.01); *C12N 15/111* (2013.01); *C12N 15/88* (2013.01); *C12Q 1/68* (2013.01); *C12N 2310/14* (2013.01); *C12N 2320/32* (2013.01)

(58) Field of Classification Search
USPC .......................... 536/23.1, 24.3, 24.5; 514/44
See application file for complete search history.

(56) References Cited

U.S. PATENT DOCUMENTS
2003/0124513 A1    7/2003   McSwiggen

FOREIGN PATENT DOCUMENTS
| CN | 1426461 A | 6/2003 |
|---|---|---|
| CN | 1948475 A | 4/2007 |
| CN | 101432432 A | 5/2009 |
| CN | 101869715 A | 10/2010 |

(Continued)

OTHER PUBLICATIONS

Jiang, Xue-yan et al. "In Vitro Study of RNA Interference on VIF Gene of HIV-1", Fudan Univ J Med Sci, vol. 36, No. 1 pp: 1672-8467 (Jan. 31, 2009); English Abstract of article.

(Continued)

*Primary Examiner* — Terra C Gibbs
(74) *Attorney, Agent, or Firm* — Thomas Engellenner; Reza Mollaaghababa; Pepper Hamilton LLP

(57) ABSTRACT

Microvesicles containing interfering RNAs, preparation methods and uses thereof are provided. Pharmaceutical compositions and kits comprising the microvesicles containing interfering RNAs are also provided. Microvesicles containing interfering RNAs, pharmaceutical compositions and kits comprising such microvesicles can be used to study the effects of interfering RNAs on receptor cells. As microvesicles containing interfering RNAs can stably, high efficiently and specifically deliver interfering RNAs, microvesicles containing interfering RNAs can be used to treat related diseases.

18 Claims, 7 Drawing Sheets

(56) References Cited

FOREIGN PATENT DOCUMENTS

| WO | 200182958 A2 | 11/2001 |
| WO | WO2005032561 A1 | 4/2005 |
| WO | 2005121369 A2 | 12/2005 |
| WO | 2007126386 A1 | 11/2007 |
| WO | 2009100029 A1 | 8/2009 |
| WO | 2009147519 A1 | 12/2009 |
| WO | WO-2009-147519 * | 12/2009 |
| WO | 2010111522 A2 | 9/2010 |

OTHER PUBLICATIONS

Wullner, Ulrich et al. "Targeted Delivery of Short Interfering RNAs—Strategies for In Vivo Delivery", Recent Patents on Anti-Cancer Drug Discovery, 4, pp. 1-8 (2009).

Simpson, Richard J. et al. "Exosomes: Proteomic Insights and Diagnostic Potential", Expert Review of Proteomics, Future Drugs, London, GB, vol. 6, No. 3, pp. 267-283 (Jun. 1, 2009).

Supplementary European Search Report for EP 10852044.6 dated Dec. 6, 2013, date of completion Nov. 29, 2013.

International Search Report Written Opinion for corresponding PCT Application PCT/CN2010/073262 date of mailing Jan. 13, 2011, date of completed Dec. 20, 2010.

International Search Report for PCT Application PCT/CN2010/079602 date of mailing Mar. 17, 2011, date of completion Feb. 17, 2011.

Office Action dated Jan. 12, 2016 for corresponding U.S. Appl. No. 13/700,062.

* cited by examiner

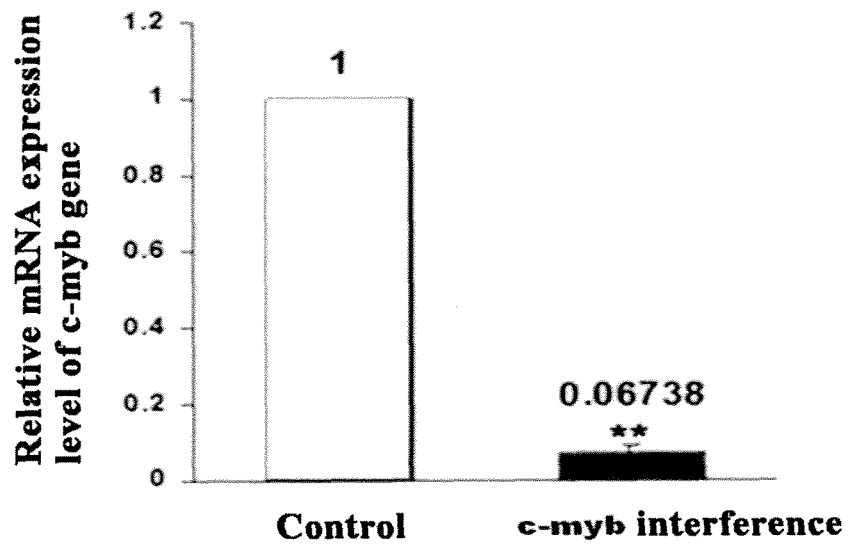
Figure 2-A
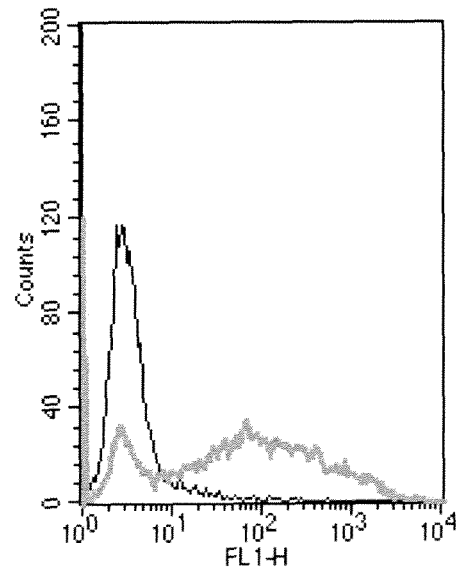
Figure 2-B

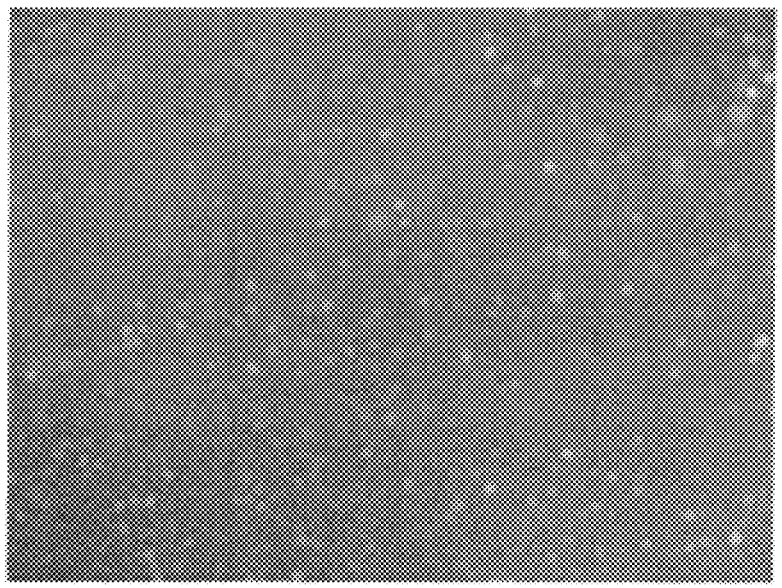
Figure 2-C
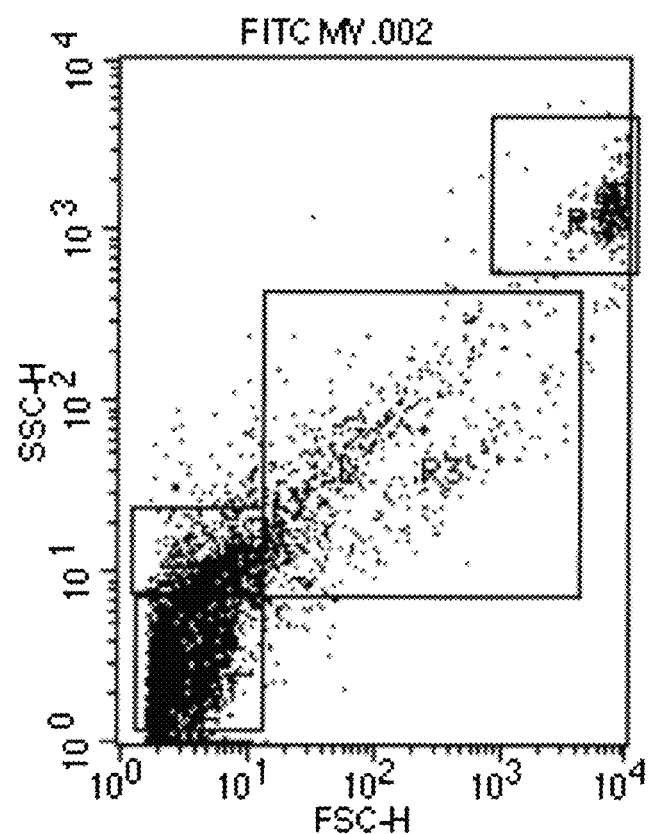
Figure 3-A

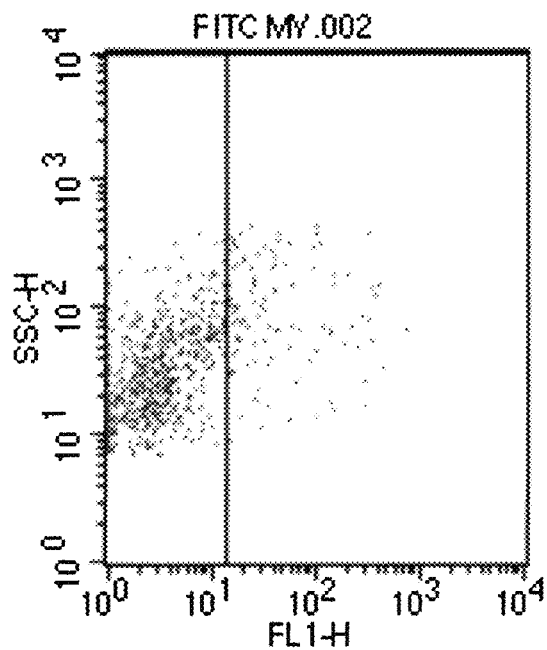
Figure 3-B
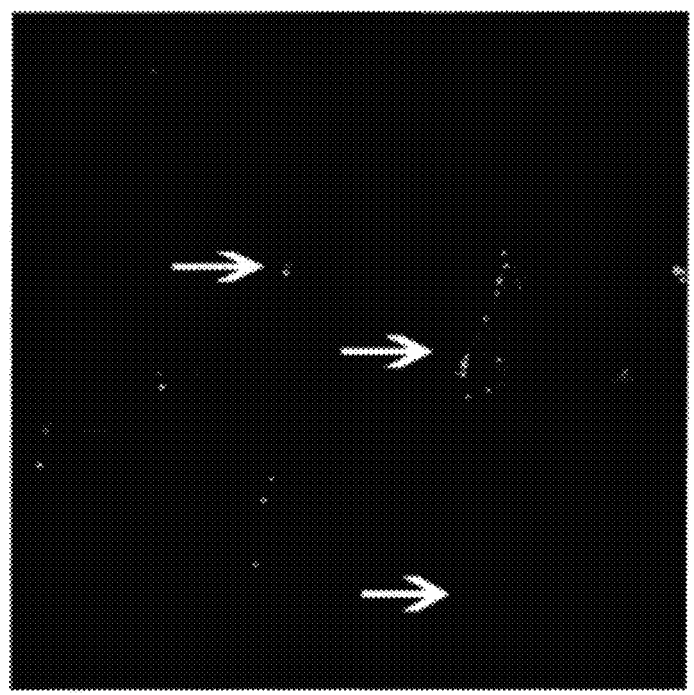
Figure 3-C

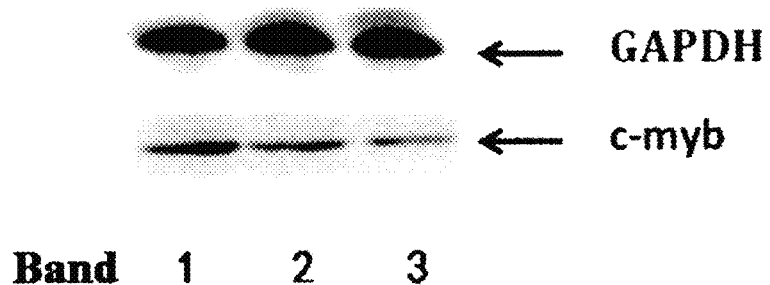
Figure 4-A
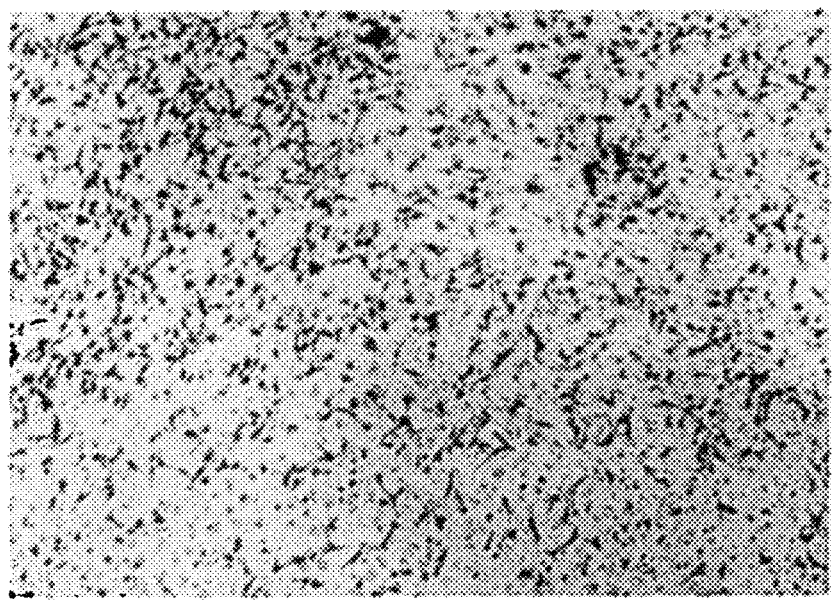
Figure 4-B

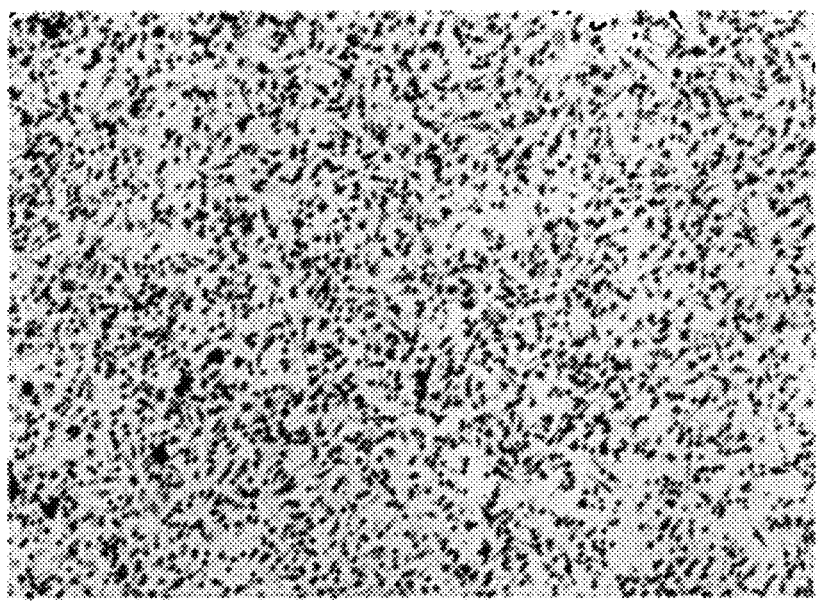
Figure 4-C
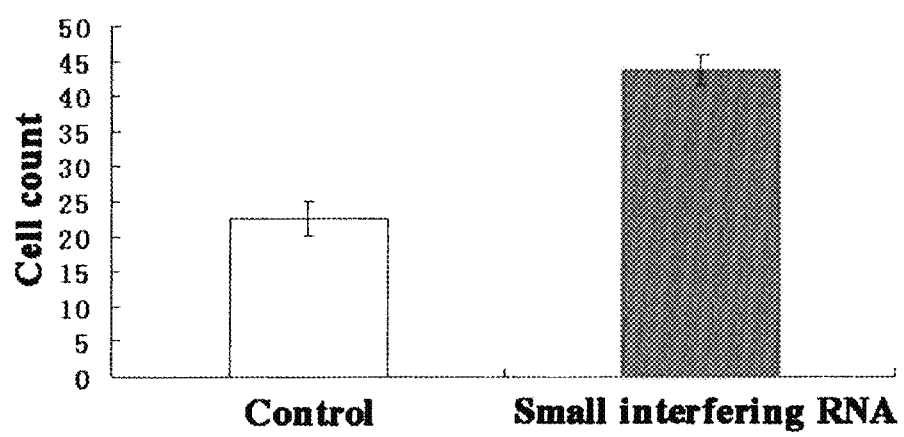
Figure 4-D

SEQUENCE LISTING

```
<160> NUMBER OF SEQ ID NOS: 2

<210> SEQ ID NO 1
<211> LENGTH: 49
<212> TYPE: DNA
<213> ORGANISM: Homo sapiens

<400> SEQUENCE: 1
ggtggaacag aatggaacat tgaacaagtg ttccattctg ttccacctt            49

<210> SEQ ID NO 2
<211> LENGTH: 49
<212> TYPE: DNA
<213> ORGANISM: Artificial Sequence
<220> FEATURE:
<223> OTHER INFORMATION: Synthetic

<400> SEQUENCE: 2
gacttcataa ggcgcatgct tgaagaaggc atgcgcctta tgaagtctt            49
```

MICROVESICLES CARRYING SMALL INTERFERING RNAS, PREPARATION METHODS AND USES THEREOF

FIELD OF THE INVENTION

The present invention relates to cellular microvesicles carrying interfering RNAs, preparation methods and uses thereof. More particularly, the invention relates to provide cellular microvesicles carrying interfering RNAs, a method of loading the interfering RNAs on cellular microvesicles and uses in the improvement of bio-medical experimental technique and in the prevention/treatment of a disease thereof.

BACKGROUND ART

Cellular microvesicles (MVs) are a category of biological vesicles with a lipid bi-layer membrane, ranging between 10-500 nm in size. They were first reported as early as in year 1967 and named "platelet dust" since they were derived from platelets, contain vesicles and have a role in promoting coagulation. In vitro studies, it has found that each of endothelial cells, vascular smooth muscle cells, platelets, leucocytes, lymphocytes, erythrocytes, and the like are all able to release MVs. According to their source, MVs can be divided into two categories: exosomes and shedding vesicles. Exosomes are secreted in the manner of exocytosis with multi-vesicular bodies (MVBs) in the case of cells are stimulated, and shedding vesicles are directly secreted from the cell surface by budding. Presently, different names are given to shedding vesicles secreted by different cells, for example, those from neutrophil granulocytes and monocytes are called ectosomes, and those from platelets are called microparticles.

Membrane component of cellular MVs, depending on the cells from which they originate, is mainly composed of lipid and protein. However, the inner component of cellular MVs is still unknown. The plasma membrane of cellular MVs contains the features of its original cells, i.e. contains specific molecular markers and cell receptors/ligands on the surface of the original cells. Definite physiological functions of cellular MVs have not been investigated clearly up to now.

Interfering RNA (siRNA) is a kind of double-stranded RNA molecule consisting of more than 20 nucleotides, and it plays a role in silencing gene expression through the specific degradation of messenger RNA (mRNA). This process is called RNA interference (RNAi).

RNAi is a way of post-transcriptional gene silencing, and is one of the old and evolutive highly conserved phenomena in the living nature. Through siRNA mediated recognition and targeting cleavage of homologous target mRNA, gene expression is suppressed specifically and efficiently. RNA interference has the characteristics of biocatalytic reaction, in which multiple proteins and ATP were involved.

In recent years, study of RNA interference has made breakthroughs, has been rated as one of the top ten most scientific progress by the journal Science in 2001, and has been ranked the top ten most scientific progress in 2002. By using RNA interfering technology, the expression of the specific gene can be knocked out or turn off. Therefore, the RNA interfering technology has been widely used in the fields of bio-medical experiment research and gene therapy of various diseases.

Before the RNA interfering technology appearing, gene knockout is the major research tool in reverse genetics, but with high difficulty of technology, complex operation and long time of research. RNA interference has been now an important research tool for exploring the function of genes due to it could use siRNA or siRNA expression vector with faster, cheaper, simply and highly sequence-specific to silence the specific gene specifically to obtain the mutation sequence with lost or decreased function so as to knockout the expression of target gene specifically. In the study of functional genomes, specific gene needed to be functional-loss or mutation sequence reduction so as to confirm its function. Therefore, RNAi can be used to the study of functional genomes as a powerful study tool. Meanwhile, the establishment of the method for construction of siRNA expression library enables the high throughput screening using RNAi technology, it has important significance in both clarification of signal transduction pathway and discovery of new drug targets.

RNAi is also wildly used in the field of treatment of diseases. In the stud of gene therapy for HIV-1, Hepatitis B and Hepatitis C etc. using RNA interference technology, it is found that selecting sequence in the viral genome that has no homology to sequences in the human as the suppression sequence can void the side effect on the normal tissues while inhibiting the replication of virus. At the same time, choosing the suppression sequence at the special would induce apoptosis of some malignant cells with definite gene mutation. Moreover, tumor cells can be killed specifically by introducing the expression of siRNA or shRNA for some oncogenes or molecules against apoptosis using the promoters specific for tumors.

As RNA interference is the gene silencing against prost-transcriptional stage, corresponding to the gene knockout genetically with traditional gene therapy, RNAi is more simply in the whole process design, and the action is rapid and effect obviously, which opens a new way for the gene therapy. The general idea is that through strengthening the mechanism of RNA interference of the key gene, to control the abnormal progress of protein synthesis appearing in diseases and replication or expression of exogenous pathogenic nucleic acid, especially some nucleic acid viruses seriously harm to human health by strengthening the mechanism of RNA interference of the key gene.

In recently, studies have demonstrated that siRNA can inhibit the replication of HIV in the cells cultured in vitro. HIV infection could be prevented by siRNA through inhibit its own gene (e.g. pie, gag, rev, tat and env) of HIV virus and its host gene (e.g. CD4, major receptor of HIV). Meanwhile, studies have found that siRNA inhibiting Fas is injected intravenously into the mouse in two mouse models with autoimmune hepatitis, it is observed that Fas mRNA and protein level in liver cells is reduced, thus preventing liver cells from damages of apoptosis caused by autoimmune hepatitis. Moreover, studies have found that transformation of tumor cells from benign to malignant can be inhibited by silencing p53 gene through RNAi.

Although RNAi has been widely used in every aspects of bio-medical research, there are still some problems difficult to be solved. For example, the efficiency of transferring siRNA to some cells, e.g. immune cells, is very low using the existing transfection method of liposome, which will affect further application of it in this field.

Meanwhile, although many achievements were made in the research and development siRNA drugs, it still faces many problems for applying it into real medical treatment. Although siRNA can be directly injected into the animals, the half life of the siRNA without encapsulating is very short, and the therapeutic efficacy is barely satisfactory. Presently, the carriers of delivering siRNA drugs mainly include liposomes, nanocapsules/nanoparticles, β-cyclodextrin inclusion compound (or also called β-cyclodextrin capsule) and so on. These carriers can partly prolong the retention time of the drugs in vivo and increase the absorption rate siRNA drug, but the targeting and high efficiency of delivering drugs are still weak. Problems of how to effectively administration to human while ensuring the drug release of the efficacy at target tissues and organs as well as having higher safety and the like are all needed to further investigation.

As an important bio-medical research tool and a potential drug, siRNA is now facing some open problems, and the poor specificity (targeting), less stability and lower efficiency of delivering siRNA are the main reasons for limiting its use. Therefore, it is an urgent need for a more stable, high effective and specific way of delivering siRNA to deliver siRNA high effectively and specifically.

It is unexpectedly for the applicant that cellular MV is a vector of bio-vesicle vehicle with highly effective rate and specificity in vivo. These cellular MVs are variable in size, ranging between 10-500 nm. In principle, the membrane components (including specific surface receptors and membrane lipid structures) of MVs secreted by different cells are the same as the plasma membrane components of the corresponding cells. Therefore, cellular MVs carrying with receptor proteins or membrane lipid structure from the surface of the cells, have high affinity to the corresponding target cells. Using cellular MVs as a carrier for delivering siRNA, siRNAs can be selectively delivered into the target cells/tissues high efficiently and selectively, thus enhancing the regulation of cellular functions greatly. It is obviously that since the cellular MVs (including the membrane lipid vesicular structures with characteristics similar to the cellular MVs, such as exosomes and shedding vesicles as well as particular shedding vesicles secreted by different cells) themselves have the specificity of binding to particular tissues and cells, the siRNA carried by cellular MV also exhibit high targeting, stability and efficiency, they have a significant application prospect in the study and therapy of the mechanism of diseases.

The inventors of the present invention find that using the cellular MV as a vector to deliver the interfering RNA to the target cells will not harm to organisms themselves, due to the cellular MV are substances secreted by cells themselves and have bio-affinity; meanwhile, cellular MVs can be transferred into the target cells efficiently and selectively due to the surface of which carry surface molecules originating from cells and have high affinity to the target cells. The interfering RNA can functions by combined with specific sequence of target gene mRNA to block the translation process of protein of the target gene, thus playing a role blocking the gene expression specifically.

The advantages of using cellular MVs as a vector to deliver siRNA are: firstly, cellular MVs originate from cells, and is a native existence of organism, thus it can overcome the toxicity to cells and damage to the body of the drug carriers presently synthesized; secondly, various technical ways used during enclosing siRNA into cellular MVs are all easy to implement and the enclosing efficiency is very high, which increase its application potential in practical to a certain degree; more importantly, cellular MV are vesicle structures with a lipid bi-layer membrane and the structure of the outer membrane is similar to that of cytoplasm, which can enter the cell through fusion with the cell membrane and endocytosis. Meanwhile, cellular MVs would enter the target cells efficiently and selectively due to its surface carrying with molecule markers such as surface protein and various receptors/ligands originating from the surface of the cytoplasm of cells. If using the cellular MVs excreted from the primary culture of tissues or cells of patients themselves to enclose siRNA, immune rejection can be reduced and the transferring efficiency of the cellular MVs carrying siRNA to organism can be further improved. Based on the above-mentioned advantages, as a carrier to deliver the siRNA as a drug, cellular MVs will play a more important role in the development of drugs and prevention and treatment of the clinical diseases.

SUMMARY OF THE INVENTION

The present invention provides cellular MVs containing siRNA.

The present invention also provides a pharmaceutical composition, which comprises cellular MVs containing siRNA and a pharmaceutically acceptable vehicle.

The present invention further provides a kit, wherein the kit includes cellular MVs containing siRNA or a pharmaceutical composition comprising cellular MVs containing siRNA, and instructions for use.

In addition, the present invention also provides a method for preparing cellular MVs containing siRNA, comprising the following steps:
transferring interfering RNA (siRNA) into cells using the cell transfection technology; or transferring siRNA into cells using the viral vector method;
separating cellular MVs containing siRNA.

The present invention also provides a research method, including:
transferring siRNA and its control sequence into donor cells, preferably by transfection or viral vector method;
separating cellular MVs containing siRNA;
adding the cellular MVs containing siRNA into a receptor, preferably receptor cells;
studying the effect of MVs containing siRNA after they enter receptor cells.

The present invention also provides a method for preventing and or treating diseases, including: transferring cellular MVs containing siRNA into a receptor.

The present invention also provides the use of cellular MVs containing siRNA in the transportation of siRNA.

DESCRIPTION OF THE DRAWINGS

FIG. 2-A shows the interference efficiency of siRNA of c-myb gene detected by Real time-PCR.

FIG. 2-B shows the results of transfection efficiency detected by flow cytometry.

FIG. 2-C shows the results of transfection efficiency detected by fluorescence microscope.

FIG. 3-A shows the detection of cellular MVs by flow cytometry.

FIG. 3-B shows the detection of cellular MVs containing siRNA by flow cytometry.

FIG. 3-C shows transferring siRNA into the target cell using the cellular microvesicle as a carrier.

FIG. 4-A shows the specific down-regulation of the expression of target protein in the target cell with siRNA.

FIG. 4-B shows the effect of cellular MVs which do not comprise siRNA on the migration ability of the target cell.

FIG. 4-C shows the effect of cellular MVs containing siRNA on the migration ability of the target cell.

FIG. 4-D shows the statistical results of the effect of cellular MVs containing siRNA on the migration ability of the target cell.

DETAILED DESCRIPTION

Cellular MVs Containing Interfering RNA

Figure 1:
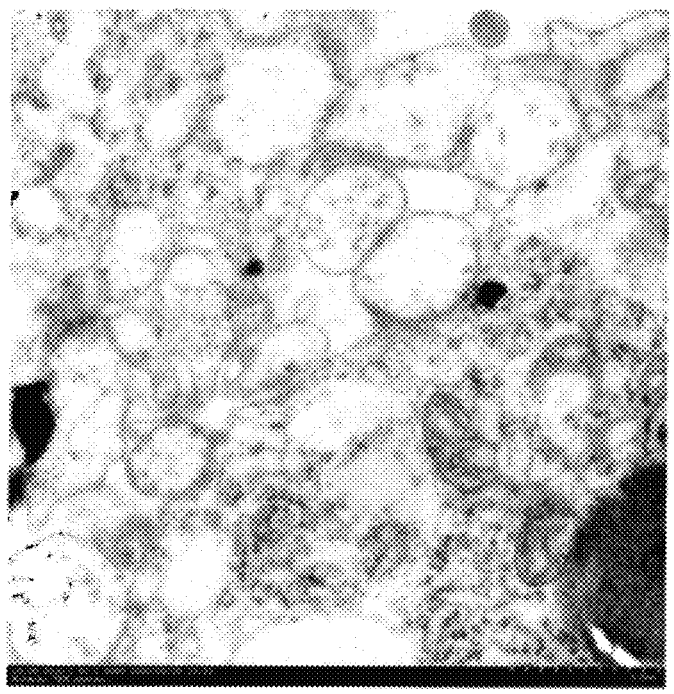
FIG. 1 shows a transmission electron microscope (TEM) picture of cellular MVs of healthy human plasma/serum.

Cellular microvesicles (MVs) are a category of natural biologic vesicles with a lipid bi-layer membrane, which is excreted from cells, ranging between 10-500 nm in size, including Exosome excreted from Multivesicular bodies (MVBs), shedding vesicles excreted by cell budding and particular shedding vesicles secreted by different cells.

Cellular MVs include any MVs produced by various cells obtained from human or animals, especially including cells of healthy or diseased human or animals which may be primary cultures or subcultures (cell lines), such as endothelial cells, vascular smooth muscle cells, platelets, leucocytes, lymphocytes and erythrocytes.

SiRNA includes all the siRNA sequences designed for receptor genes, which will degrade the target genes specifically through the mechanism of RNAi.

The present invention provides a pharmaceutical composition and a kit that can be used for the treatment of a disease.

According to one embodiment of the present invention, there is provided a pharmaceutical composition, comprising cellular MVs containing siRNA and pharmaceutically acceptable vehicles. The pharmaceutically acceptable vehicles include, for example normal saline, serum, cell culture medium, phosphate buffer solution (PBS), etc.

According to one embodiment of the present invention, there is provided a kit, wherein the kit includes cellular MVs containing siRNA or a pharmaceutical composition comprising cellular MVs containing siRNA, and instructions for use.

Diseases that can be prevented or treated with cellular MVs containing siRNA or a pharmaceutical composition comprising cellular MVs containing siRNA or a kit include: various tumors; various acute and chronic infectious diseases, for example viral diseases such as viral influenza, viral hepatitis, AIDS, SARS, bacterial diseases such as tuberculosis, bacterial pneumonia, and other acute and chronic infectious diseases caused by various pathogenic microorganisms; other acute and chronic diseases, such as respiratory system diseases, immune system diseases, blood and hematopoietic system diseases, circulatory system diseases, endocrine system and metabolic diseases, digestive system diseases, nervous system diseases, urinary system diseases, reproductive system diseases and motor system diseases.

Methods

In addition, the present invention also provides a method for preparing cellular MVs containing siRNA, including the following steps:
transferring interfering RNA (siRNA) into cells using the cell transfection technology; or transferring siRNA into cells using the viral vector method;
separating cellular MVs containing siRNA.

The method for preparing cellular MVs includes, e.g., differential centrifugation, immune adsorption and ultrafiltration.

Preferably, the cellular MVs are prepared with differential centrifugation which comprises, for example, the following steps: firstly, centrifuging the body fluid, blood, cells, tissues, cells or tissues cultured in vitro to remove all kinds of cells and fragments; then ultracentifugating the supernatant to get the precipitates which are cellular MVs.

Or alternatively, preferably the cellular MVs are prepared with immune-adsorption which comprises, for example, the following steps: (1) firstly, centrifuging the body fluid, blood, cells, tissues, cells or tissues cultured in vitro to remove all kinds of cells and fragments to get the supernatant; (2) incubating cell-specific antibodies or immunemagnetic beads (Invitrogen, US) absorbed on the tissue culture dish with the supernatant (e.g., for 30-60 min) to achieve the absorbed cellular MVs.

Or alternatively, preferably the cellular MVs are prepared with for example ultrafiltration including following steps:
(1) firstly, centrifuging the body fluid, blood, cells, tissues, cells or tissues cultured in vitro to remove all kinds of cells and fragments to get the supernatant; (2) centrifuging the supernatant in an ultrafiltration centrifuge tube with a 100 KDa MWCO (Millipore, US) at 4000 rpm, concentrating to achieve cellular MVs.

Preferably, the present invention provides a method for preparing cellular MVs containing siRNA. The MVs can be transferred into the receptor cells or organisms efficiently and specifically, and interfere with the expression of protein of the target genes by siRNA.

According to one embodiment of the invention, the method includes:
1) enclosing siRNA in microvesicles of the donor cells;
2) separating the cellular MVs excreted by donor cells;
3) detecting the loading efficiency of siRNA in the cellular IVs;
4) transferring the cellular MVs containing siRNA into receptor, for example receptor cells, preferably by injecting into organisms.

According to another embodiment of the invention, the method for preparing cellular MVs containing siRNA comprises:
1) designing siRNA sequence for target gene;
2) synthesizing mature siRNA or constructing siRNA expression vector chemically.
3) transferring siRNA or siRNA expression vector into cells through using cell transfection technology.

Preferably, the siRNA sequence of target gene is designed with the following principles:
(1) siRNA fragment meets AAN19TT, NAN19NN, NARN17YNN and NANN17YNN (N represents any base, R and Y represent purine and pyrimidine respectively);
(2) selecting complementary DNA exon sequences without repeated sequences and antisense strand with balanced content of A, G, C, T (or the content of GC is between 30% and 70%);
(3) avoiding the sequences with clustered single bases, especially G base;
(4) avoiding untranslated regions of 3' and 5' ends (5'-UTR, 3'-UTR) which usually are binding sites of mRNA binding protein.
(5) avoiding the start codon or exon-exon boundaries.

The designed siRNA sequence is researched for BLAST in EST or Unigene data base of NCBI (National Center for Biotechnology Information) to ensure the specificity of the siRNA sequence to the target gene.

More than 4 of siRNA sequences are designed and synthesized, and then siRNA sequences with best silence effect are screened by experiment for further gene function study.

Preferably, method for the construction of siRNA expression vector includes: inserting DNA molecules with about 70 bp bases in length comprising a specific stem-loop and termination signal into a certain vector.

Preferably, method for transfecting siRNA is performed by liposome method (Lipofectamine 2000, Invitrogen).

The method for preparing cellular MVs is selected from one or more of differential centrifugation, immune-adsorption and ultrafiltration.

The method for detecting the loading efficiency of siRNA in cellular MVs is selected from one or more of RT-PCR, Real time-PCR, Northern blot, immunofluorescence and flow cytometry.

RT-PCR, for example, includes the following steps:
(1) extracting total RNA of cells or tissues after RNA interference, and cDNA samples are achieved by reverse transcription;
(2) performing PCR reactions with target gene specific primers;
(3) performing agarose gel electrophoresis of the PCR product;
(4) observing the results under UV lamp after EB staining.

Real time PCR, for example, includes the following steps:
(1) extracting total RNA of cells or tissues after RNA interference, and cDNA samples are achieved by reverse transcription;
(2) designing target gene specific primers;
(3) performing PCR reactions by adding fluorescent probes.

Northern blotting, for example, includes the following steps:
(1) collecting serum/plasma, and cell, tissue samples;
(2) extracting total RNA by Trizol reagent;
(3) performing denature PAGE and transmembrane;
(4) preparing target gene probe labeled with isotope;
(5) performing membrane hybridization;
(6) detecting the results by isotopic signals, e.g., Phosphor Scanning.

Immunofluorescence, for example, includes the following steps:
(1) attaching cells on the support;
(2) fixing cells with cell fixative, e.g., paraformaldehyde;
(3) blocking cells with skimmed milk or bovine serum albumin;
(4) labeling protein specific for target gene with fluorescent labeled antibodies;
(5) observing the fluorescence intensity of the cells under fluorescence microscope.

The receptor cells include all existing cell lines, cell strain and primary cultures of cells or tissues of healthy human or patients with diseases.

Organisms into which cellular MVs can enter include human, various animals and various pathogenic microorganisms. The animals include chondrichthyes, teleost, amphibians, reptiles, birds and mammals. The pathogenic microorganisms include bacterium, spirochetes, mycoplasma, rickettsia, chlamydia and actinomycetes. Specially, the pathogenic microorganisms include various kinds of DNA and RNA viruses, such as hepatitis B virus, smallpox virus, AIDS virus, SARS, influenza virus, etc.

The present invention also provides a research method, including:
transferring siRNA and its control sequence into donor cells;
separating cellular MVs containing siRNA;
adding the cellular MVs containing siRNA into receptor cells;
studying the effect of MVs containing siRNA after they enter receptor cells.

According to one embodiment of the invention, the method for studying the gene function using cellular MVs carrying siRNA includes:
1) transferring siRNA and its control sequence into the donor cells by transfection;
2) separating and preparing microvesicles of the donor cells containing siRNA;
3) adding the cellular MVs into receptor cells;
4) studying the effect of cellular MVs carrying siRNA on the function of receptor cells after they enter receptor cells to investigate the effect of their target genes on the function of cells.

The method for studying effect of cellular MVs carrying siRNA on the function of receptor cells after entering receptors includes one or more of confocal fluorescence microscopy, Western blotting and method of cell migration.

For example, Western blotting includes the following steps:
(1) extracting total proteins of cells or tissues with the protein lysis solution.
(2) performing SDS-PAGE and transmembrane.
(3) blocking cells with skimmed milk or bovine serum albumin;
(4) labeling protein specific for target gene on the membrane with HRP labeled antibodies;
(5) adding HRP substrate to produce luminescence reaction;
(6) radioautographing.

The present invention also provides a method for preventing and or treating diseases, including: transferring cellular MVs containing siRNA into receptor.

According to one of the embodiment of the invention, method for preventing/treating diseases using cellular MVs carrying siRNA includes:
1) transferring siRNA into donor cells by transfection;
2) separating and preparing microvesicles of the donor cells containing siRNA;
3) adding the cellular MVs into receptor cells or injecting the cellular MVs into patients.
4) cellular MVs carrying siRNA enter receptor cells or tissues of patients and change the content of protein of the target gene through interfering the expression of target genes of the receptor cells or tissues of patients.
5) cellular MVs carrying siRNA play a role in preventing/treating diseases by changing the proteins in cells to affect cellular function.

Diseases include: various tumors; various acute and chronic infectious diseases, for example viral diseases such as viral influenza, viral hepatitis, AIDS, SARS, bacterial diseases such as tuberculosis, bacterial pneumonia, and other acute and chronic infectious diseases caused by various pathogenic microorganisms; other acute and chronic diseases, such as respiratory system diseases, immune system diseases, blood and hematopoietic system diseases, circulatory system diseases, endocrine system and metabolic diseases, digestive system diseases, nervous system diseases, urinary system diseases, reproductive system diseases and motor system diseases.

SiRNA includes all the siRNA sequences designed for receptor genes, which will degrade the target genes specifically through the mechanism of RNAi.

Genes include all gene fragments which can be transcribed into molecules with function, such as protein gene, microRNA gene and so on. Disease-causing genes include various genes of organisms including human and various animals including chondrichthyes, teleost, amphibians, reptiles, birds and mammals, etc. which themselves participate in the occurrence and development of diseases.

The above-mentioned pathogenic microorganisms include bacterium, spirochetes, mycoplasma, rickettsia, chlamydia and actinomycetes. Specially, the pathogenic microorganisms include various kinds of DNA and RNA viruses, such as hepatitis B virus, smallpox virus, AIDS virus, SARS, influenza virus, etc.

The present invention also provides the use of cellular MVs containing siRNA in delivering siRNA.

EXAMPLES

It can be understood that the specific embodiments described herein are illustrated by way of examples and does not as a limitation of the invention. The main features of the present invention can be applied in various embodiments without departing from the scope of the invention. It will be realized or can be confirmed by a person skilled in the art that many equivalents can be applied to the specific steps described herein using conventional experiments. These equivalents are considered to be within the scope of the invention and covered by the appended claims.

Example 1

Separation and Detection of the Cellular MVs in the Serum/Plasma and Cell Culture Medium Differential centrifugation is used in this example to separate cellular MVs from serum/plasma or cell culture medium:
Specifically, serum/plasma or cultured cells is centrifuged under 300 g for 5 min to get the supernatant; (2) the supernatant is centrifuged under 1500 g for 20 min to get the supernatant; (3) the supernatant is centrifuged under 10000 g for 30 min to get the supernatant; (4) the supernatant is centrifuged under 110000 g for 70 min to get the precipitates which are cellular MVs.

The separated cellular MVs are observed under transmission electron microscope (TEM). Cellular MVs precipitates are fixed in 2.5% of glutaral at 4° C., overnight rinsed three times with PBS for 10 min each, then fixed in 1% of osmium tetroxide at room temperature for 60 min. The fixed samples are embedded with 10% of gelatin and then refixed with glutaral at 4° C. After that, the samples are cut into small pieces (with a volume of less than 1 mm$^3$). The samples are dehydrated with ethanol solutions of increasing concentration successively (30%, 50%, 70%, 90%, 95% and 100%×3). After embedding with epoxy resin, the samples are sliced with Leica UC6 microtome and finally observed under FEI Tecnai T20 transmission electron microscope at 120 kV.

The transmission electron microscope (TEM) picture of cellular MVs created by differential centrifugation is shown in FIG. 1. FIG. 1 shows that cellular MVs separated from healthy human serum/plasma are different in size, ranging between 10-500 nm.

Example 2

Transfection of siRNA into Donor Cells

In this example, fluorescence labeled siRNA is transfected into cells according to the following steps and the transfection efficiency is detected.

Firstly, siRNA sequence is designed for different sites of human c-myb gene sequence:
(sense strand+loop+antisense strand): 5'-GGTGGAACA-GAATGGAACATTGAACAAG TGTTCCATTCTGTTC-CACCTT-3' (SEQ ID NO:1);
Meanwhile, a random sequence is designed as the negative control:
(sense strand+loop+antisense strand): 5'-GACTTCAT-AAGGCGCATGCTTGAAGAAG GCATGCGCCTTAT-GAAGTCTT-3' (SEQ ID NO:2).

Furthermore, the above-mentioned designed siRNA is synthesized commercially, siRNA against c-myb gene is labeled with green fluorescent dye FITC.

The siRNA is transfected into human monocytes/macrophages cell line THP-1 cells (Type Culture Collection of Chinese Academy of Sciences, Shanghai, China) with liposome Lipofectamine 2000 (Invutrigen, US), the detailed method is as follows:
(1) THP-1 cells are cultured in the RPMI 1640 medium (Gibco, US) supplemented with 10% FBS (Gibco, US), 5% $CO_2$, at 37° C.
(2) 30 μl lipofectamine 2000 and 600 pmol negative control of siRNA is mixed with 1 ml OPTI-MEM (Gibco, US) respectively to form mixture A and B, then kept at room temperature for 5 min.
(3) 30 μl lipofectamine 2000 and 600 pmol c-myb siRNA is mixed with 1 ml OPTI-MEM (Gibco, US) respectively to form mixture C and D, then kept at room temperature for 5 min.
(4) mixture A is mixed with mixture B to form mixture E, kept for 20 min.
(5) mixture C is mixed with mixture D to form mixture F, kept for 20 min.
(6) mixture E and mixture F are added into the cells in control group and experimental group respectively, OPTI-MEM is added to 15 ml. Cultured with 5% $CO_2$ at 37° C.
(7) normal culture medium is refreshed after 6 h.
(8) the transfection is completed after 24-48 h, and samples can be collected.

Real time-PCR was used to detect mRNA level of c-myb gene so as to detect interference efficiency, the method includes:
(1) collecting the transfected THP-1 cells
(2) preparing cDNA sample: the total RNA is extracted with Trizol reagent (Invitrogen, US) and the cDNA samples was achieved through reverse transcription of the total RNA. The reaction system of reverse transcription contains 4 μl 5×AMV buffer solution, 2 μl 10 mM each dNTP mixture (Takara, Japan), 0.5 μl RNase Inhibitor (Takara, Japan), 2 μl AMV (Takara, Japan) and 0.5 μl OligodT (Takara, Japan). The reaction steps are that incubated at 16° C. for 15 min, reacted at 42° C. for 1 h, and incubated at 85° C. for 5 min.
(3) Real-time PCR reaction: 0.3 μl Taq enzyme (Takara, Japan), 0.5 μl 10 μm forward and reverse primers, 1.2 μl 25 mM $MgCl_2$, 1.6 μl 2.5 mM each dNTP mixture (Takara, Japan), 1 μl 20×EVA GREEN, 2 μl 10×PCR buffer solution and 12.4 μl $H_2O$ are added to 1 μl cDNA. The PCR system is 20 μl. The instrument used is ABI Prism 7300 fluorescence ration PCR instrument. The reaction condition is: 95° C., 5 min for one cycle→95° C. 15 s, 60° C. 1 min for 40 cycles.
(4) Data processing: the data processing method is $\Delta C_T$ method. $\Delta C_T$ is set as the cycle number when the reaction reached threshold. Therefore, the comparison of siRNAs in the two groups of samples can be represented by equation $2^{-\Delta C_T}$, wherein $\Delta C_T = C_{T\ group1} - C_{T\ group2}$. The data processing method of the cells and tissues is that U6 is used as an internal standard. Thus the comparison of mRNA expression in the two groups of samples can be represented by equation $2^{-\Delta C_T}$, wherein $\Delta C_T = [C_{TmiRNA} - C_{T\ U6}]_{group1} - [C_{TmiRNA} - C_{T\ U6}]_{group2}$.

The result is shown in FIG. 2-A, compared with the negative control group transfected with random sequence (left column), mRNA expression of c-myb gene in cells transfected with c-mybsiRNA decreases significantly, suggesting the feasibility and efficiency of the transfection method used in this experiment.

Meanwhile, flow cytometry is used to detect the efficiency of siRNA transferred into cells. The results is shown in FIG. 2-B. The flow cytometry includes the following steps: collecting THP-1 cells after interference and adjusting the cell concentration to $10^6$/ml; detecting the fluorescence intensity of the cells by flow cytometry (BD FACS, Calibur) with the zoom modes of voltage being lin at both forward and lateral when detection, and fluorescence intensity is detected with FL1-H with the zoom mode of voltage being log. It can be seen from the results that, compared with the control group (fine line), the fluorescence intensity of the experiment group (thick line) transfected with c-mybsiRNA increase, indicating that the transfection efficiency of siRNA is high, and such method is an intuitive and efficient one in detection of transfection efficiency of siRNA.

In addition, fluorescence microscopy method can also be used to detect the efficiency of siRNA transferring into cells, the method includes: THP-1 cells that have been transfected with c-mybsiRNA are placed on the object stage of fluorescence invert microscope (OLYMPUS) and detected with a excitation wavelength of 488 nm.

The result is shown in FIG. 2-C, after transfection, the cells show green fluorescence (as shown in the bright), suggesting that the efficiency of the siRNA transferring into the cells is high.

Example 3

Transferring of Cellular MVs Carrying with siRNA into Receptor Cells

In this example, cellular MVs of THP-1 cells transfected with c-mybsiRNA are collected to detect their loading efficiency. Meanwhile, the cellular MVs are added to target cells to detect their efficiency of transferring into the target cells.

Human monocytes/macrophages cell line THP-1, which plays an important role in the inflammatory response is selected as the study object. THP-1 cells are incubated in the 1640 medium (Gibco, US) supplemented with 10% fetal calf serum (FBS) (Gibco, US) at 37° C., 5% $CO_2$. First, the THP-1 cells transfected with c-mybsiRNA are prepared according to the method of siRNA transfection in example 2.

Next, according to the method of separating the cellular MVs in example 1, THP-1 cells transfected with c-mybsiRNA are separated.

Then, the loading efficiency of siRNA in cellular MVs separated is detected by flow cytometry.

The result is shown in FIG. 3-A. During detection, zoom modes of voltage are lin at both forward and lateral, and fluorescence intensity is detected with FL1-H and the zoom mode of voltage is log. It can be observed seen from the results that part of cellular MVs excreted by THP-1 (right part of the vertical lines in FIG. 3-B) is labeled with fluorescence. As c-myb siRNA is labeled with fluorescence, the fluorescence intensity is detected by flow cytometry could reflect the loading efficiency of siRNA in cellular MVs.

Finally, microvesicles secreted by THP-1 cells carrying c-mybsiRNA are added to the cell culture medium of human venule endothelial cells HMEC-1 (Georgia CDC, US). HMEC-1 cells are incubated in the MCDB-31 medium (Gibco, US) supplemented with 10 ng/mL epidermal growth factor (Becton-Dickinson, US), 10 ng/mL hydrocortisone (Sigma) and 10% FBS (Gibco, US) at 37° C., 5% $CO_2$.

Under the physiological condition, monocytes/macrophages cells can interact with vascular endothelial cells. Molecules on the surface of monocytes can specifically bind to the receptors/ligands on the surface of endothelial cell, thus inducing a series of signal transduction as well as activity of cell physiology. Therefore, monocytes/macrophages cell line THP-1 and human venule endothelial cells HMEC-1, the interaction of these two kinds of cells in vivo can be simulated.

The transferring efficiency of THP-1 microvesicle carrying siRNA into HMEC-1 cells is detected. Due to the cellular microvesicles are labeled with green fluorescence, the fluorescent result of HMEC-1 is detected by fluorescence microscopy, which would reflect the transferring efficiency of MVs into HMEC-1. The result is shown in FIG. 3-C.

From the result, it can be seen that cellular MVs carrying siRNA could enter target cells HMEC-1 (bright point in FIG. 3-C) efficiently and specifically. As all cells could excrete cellular MVs like hemocyte; and all cells could receive cellular MVs excreted by the cells which could specifically act on them. Consequently, the action mode of THP-1 cellular MVs entering into HMEC-1 cells can also simulate the one all cellular MVs entering into their target cells on the organism.

According to the above-mentioned results, it is not difficult to find that cellular MVs are ideal vectors that transfer siRNA stably, efficiently and specifically, which may transfer siRNA to its receptor cells through cellular MVs. It is suggested that siRNA can be high-affinity and specifically delivered as a drug to target cells through microvesicles, and the purpose of drug prevention/treatment can be achieved by affecting the function of target cells involving in developing disease.

Example 4

Study of the Gene Function with Cellular MVs Carrying siRNA

In this example, cellular MVs were used to transfer siRNA against target genes to receptor cells efficiently and specifically, which, by specifically reducing the expression of target gene in receptor cells, simulate the pathological conditions or plays an action of gene knockout, so as to study the physiological functions of target genes in cells.

In this example, c-myb gene is selected as the study object, which encodes a cell transcription factor and plays an important role in cell differentiation, proliferation, migration and survival of hemocyte. C-myb has been proven to be an important proto-oncogene and has a close relation to the occurrence and development of a series of cancers.

In order to study the function of c-myb gene in endothelial cells, the following experiment is designed:
1) preparing the THP-1 cells transfected with c-myb siRNA according to the transfection method of siRNA in example 2.
2) separating the THP-1 cells transfected with c-myb siRNA according to the separation method of cellular MVs in example 1.
3) Adding the cellular MVs carrying c-mybsiRNA to the culture medium of HMEC-1 cells and collecting cells after 6 h to perform Western blot. The detailed steps include:
    (1) extracting total protein with the protein lysis solution;
    (2) performing SDS-PAGE electrophoresis under constant pressure of 90V;
    (3) carrying out membrane-transferring experiment under constant current of 160 Ma;

(4) blocking the membrane with 5% skim milk;
(5) labeling c-myb and GAPDH with monoclonal antibodies against anti-c-myb (Santa Cluz Co., LTD) and monoclonal antibodies against anti-GAPDH (Santa Cluz Co., LTD) respectively;
(6) adding the corresponding HRP to label the secondary antibody;
(7) adding the substrate of HRP to trigger luminescence reaction.
(8) autoradiographing.

By combining with the target gene mRNA of siRNA and recruiting the silencing complex in the cells, the target gene mRNA of siRNA are degraded, thus leading to the decrease of the expression level of its target protein. Therefore, the efficiency of siRNA entering the receptor cells can be detected by Western blot which detect the expression level of the specific protein.

The result is shown in FIG. 4-A. It can be seen from the result that, as an internal reference standard, GAPHD has demonstrated that the amounts of the total proteins added during Western blot are the same in all of the bands. Meanwhile, compared with the cells transferred with negative control (band 2), the expression level of c-myb protein have decreased significantly in the cells transferred with c-myb siRNA (band 3). Therefore, it has been proven by the inventors that: c-myb siRNA carrying cellular MVs is delivered to HMEC-1 cells and has an interference effect on the expression of the c-myb protein in HMEC-1 cells. It is further demonstrated that siRNA can be delivered to the target cells efficiently and specifically, which, as a experimental tool, study the function of the genes in specific cells.

At the same time, effect of siRNA carried by MVs on the migration ability of its target cell HMEC-1 is also detected in example 1.

As an important transcription factor, c-myb gene plays an important role in cell growth, migration, and differentiation. Though researches have proven that c-myb has significant regulatory effect on the migration of various kinds of cells, which it plays a role in the migration of endothelial cells still needs further investigation.

So in this example, the expression of c-myb protein in endothelial cell line HMEC-1 cell is reduced specifically by using siRNA carried by cellular MVs in this example to detect the migration function of cells under this condition, thus studying whether the c-myb gene has an effect on migration function of endothelial cells The detailed experimental steps include:
(1) preparing the THP-1 cells transfected with c-myb siRNA according to the transfection method of siRNA in example 2.
(2) separating the THP-1 cells transfected with c-myb siRNA according to the separation method of cellular MVs in example 1.
(3) incubating the HMEC-1 cells for 2 h with THP-1 cellular MVs carrying with c-mybsiRNA.
(4) detecting the migration ability of HMEC-1.

The detection method of the cell migration experiment include: covering polycarbonate membrane (8 μm in pore diameter) at the bottom of the upper small chamber on Transwell Boyden Chamber (6.5 mm, Costar, Cambridge, Mass., US) with 0.1% gelatin; suspending the HMEC-1 cells in medium without serum at a concentration of $(1-10) \times 10^5$ cells/mL; incubating the cells with or without the cellular MVs containing siRNA derived from THP-1 for 2 h, then adding the HMCE-1 cells on the upper small chamber, while adding 0.5 mL of medium with 10% FBS to the lower small chamber; incubating in incubator with 5% $CO_2$ for 4 h; fixing the cells migrated to the lower layer with 90% ethanol at room temperate for 15 min; washing; staining with 0.1% crystal violet at room temperate for 15 min; scraping down the cells remained on the filter membrane; photographing (Olympus, BX51, Japan); count the cells.

The microscopic picture of cells after migration is shown in FIG. 4-B\C\D. It can be seen from the results that, compared with the negative control (FIG. 4-B), the migration ability of HMCE-1 cells treated with cellular MVs carrying c-myb siRNA increases significantly. Number of cells is counted in 5 random visual fields, the result is shown in FIG. 4-D. The number of migrated cells of HMEC-1 cells which are treated with cellular MVs carrying c-myb siRNA increases significantly in compared with the control.

So, migration ability of HMEC-1 cells can be enhanced significantly by c-myb genes with lower expression. Instead, it is therefore suggested that c-myb gene has inhibitory effect on the migration of endothelial cells.

Thus in this example, it has been proven that preparing cellular MVs carrying siRNA and relative method can be used as a study tool of medical biology, to study the function of the genes by selectively decrease the expression of certain genes in the cells.

Example 5

Prevention/Treatment of Diseases with Cellular MVs Carrying siRNA

In this example, cellular MVs carrying siRNA against HIV gene are used to inhibit the survival and reproduction of HIV in its host cells.

The detailed method includes the following steps:
1) designing siRNA sequence for HIV genomic sequence;
2) inserting siRNA sequence into a vector;
3) transfecting the vector carrying HIV siRNA into the donor cell 293T cell;
4) collecting the cellular MVs excreted by donor cells;
5) adding the cellular MVs containing HIV siRNA excreted by donor cells to the HIV host cells;
6) detecting the content of viruses in host cells.

Figure 5:
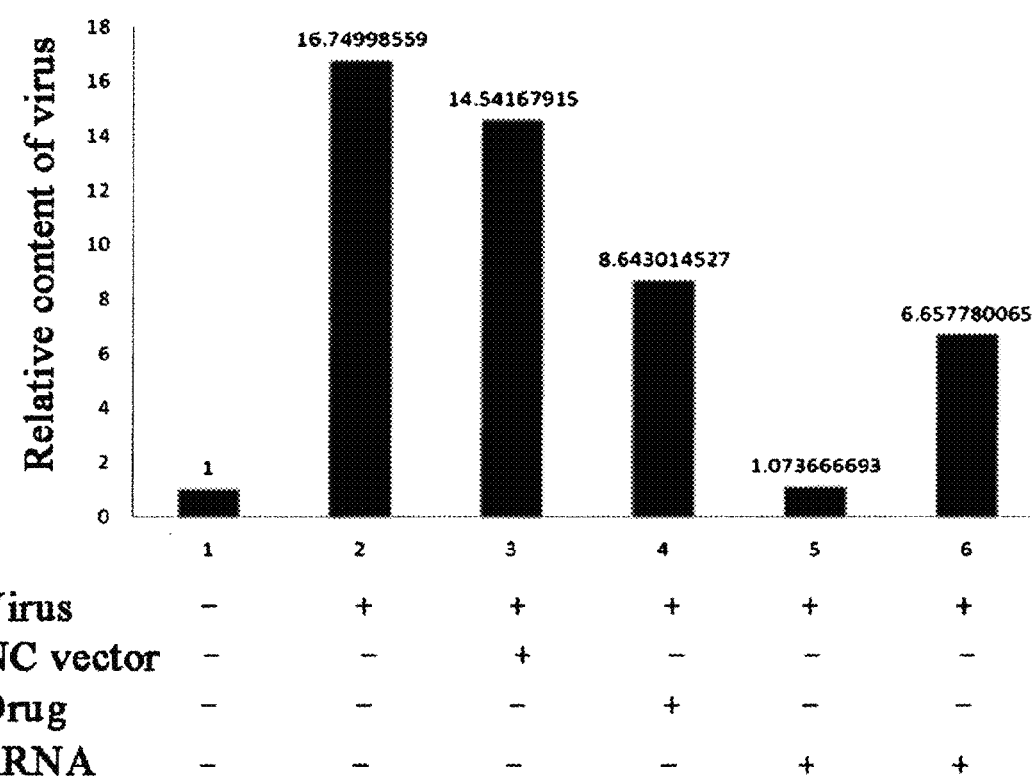
FIG. 5 shows the inhibitory effect of cellular MVs containing siRNA on the HIV.

The result is shown in FIG. 5. The ordinate represents the content of HIV in their host cells. If the blank cells completely freed of viruses are used as the control (horizontal axis 1 represents the column), its value is set to be 1; The content of viruses in cells only with viruses but without any therapeutic measures (horizontal axis 2 represents column) will be more than 16 times of the control cells. However, if the cellular MVs carrying viruses siRNA are used as the treatment tool, the content of viruses in the host cells will dramatically decreased. It can be seen from the result that, after the siRNA carried by cellular MVs is added (horizontal axis 5 and 6 represent columns), the content of viruses in host cells reduces to about 40% (horizontal axis 6 represents column). More importantly, if the content of siRNA carried by MVs (horizontal axis 5 represents column), the HIV in host cells can even be totally inhibited, and the content of HIV can decreases to level equal to that of the non-viruses group (horizontal axis 1 represents column).

Furthermore, in order to exclude the inhibitory effect of the cellular MVs carrying siRNA on HIV is caused by the vector itself and not siRNA, we have also transferred the blank control without siRNA as another control (horizontal axis 3 represents column). It can be seen from the result that only the blank vector can not have inhibitory effect on the HIV, which has also demonstrated that it is siRNA itself and not the vector that have inhibitory effect on the viruses.

Meanwhile, we have also added a anti-HIV drug with short peptides as the positive control (horizontal axis 4 represents column). It is observed from the result that the content of HIV content can only be reduced to about 50% by the drug. Therefore, in compared with the conventional drugs for treating AIDS, the cellular MVs carrying HIV siRNA has higher efficiency and better effect of inhibiting viruses. It is further suggested that using the cellular MVs carrying siRNA to treat diseases has great development potential.

Example 6

Detection of Pharmaceutical Composition Consisting of Cellular MVs and siRNA Carried Thereof In this example, a series of methods are used to detect the existence of cellular MVs and pharmaceutical composition composed of siRNA carried by cellular MVs.
  (1) The fluorescence-labeled siRNAs are transfected into donor cells according to the method described in example 2. The result is shown in FIG. 2-C, it is observed under fluorescence microscope that fluorescence-labeled siRNA had been transfected into cells.
  (2) Cellular MVs, excreted by donor cells transfected with fluorescence-labeled siRNA, are separated and identified according to the method described in example 1. The result is shown in FIG. 1. It is observed that the separated and obtained cellular MVs comply with the characteristics of cellular MVs from the shape, size and membrane structure, etc.
  (3) Flow cytometry is used to detect if there are any siRNA enclosed in the microvesicles which had already been separated and purified as well as identified as cellular MVs, i.e. if they make up complex of cellular MVs and siRNA, the result is shown in FIG. 3-B. Due to siRNA is labeled with fluorescence, if siRNA is contained in cellular MVs, the cellular MVs must be labeled with fluorescence. Therefore, we use the flow cytometry to detect the content of fluorescence carried by cellular MVs. As it is shown in FIG. 3-B that, most of the cellular MVs carry with fluorescence (right part of the vertical lines in FIG. 3-B), which proves siRNAs are enclosed in cellular MVs, i.e. proves the existence of cellular MVs-siRNA drug complex.

The present invention provides, including: (1) cellular MVs carrying siRNA; (2) the treatment of various clinical diseases (including: various tumors; acute and chronic infectious diseases and other acute and chronic infectious diseases caused by various pathogenic microorganisms; other acute and chronic diseases, such as respiratory system diseases, immune system diseases, blood and hematopoietic system diseases, e.g., circulatory system diseases of cardiovascular and cerebrovascular diseases, endocrine and metabolic system diseases, digestive system diseases, nervous system diseases, urinary system diseases, reproductive system diseases and motor system diseases) are researched using siRNA carried by cellular MVs; (3) functions of specific genes are researched using the cellular MVs which highly and specifically deliver the siRNA as a experimental tool.

According to a series of studies mentioned above, it is clearly that the present invention provides a method for preparing cellular MVs carrying siRNA, which has a highly targeting property, stability and high efficiency.

According to the above-mentioned method, the present inventor has confirmed that siRNA could be delivered to target cells by cellular MVs stably, efficiently and specifically, and influence the functions of the target cells by acting on their target genes. Therefore, the cellular MVs carrying siRNA, can not only act as a bio-medical research tool, playing a role in the study of the gene function; also act as a drug, entering the organisms efficiently and specifically, playing a role of changing the gene expression and influencing the cell functions, thus treating/preventing diseases.

What is claimed is:

1. Cellular microvesicles comprising small interfering RNAs (siRNA), wherein the cellular microvesicles are selected from the group consisting of THP-1 cellular microvesicles carrying a c-myb siRNA and 293T cellular microvesicles carrying a HIV siRNA.

2. The cellular microvesicles according to claim 1, wherein the cellular microvesicles are obtained from donor cells of human or animals.

3. The cellular microvesicles according to claim 2, wherein the donor cells include cell lines or primary cultures.

4. The cellular microvesicles according to claim 1, wherein the small interfering RNAs are enclosed in the cellular microvesicles.

5. The cellular microvesicles according to claim 1, wherein a mean diameter of the cellular microvesicles is in the range of 10-500 nm.

6. The cellular microvesicles according to claim 1, wherein the cellular microvesicles include at least one of an exosome, a shedding vesicle and other biological vesicles originating from cells.

7. A kit including the cellular microvesicles containing interfering RNAs according to claim 1.

8. A pharmaceutical composition, comprising the cellular microvesicles containing interfering RNAs according to claim 1.

9. A method for preparing the cellular microvesicles comprising small interfering RNAs (siRNA) of claim 1, comprising the following steps: transferring a c-myb siRNA into THP-1 cells or transferring a HIV siRNA into 293T cells; and separating the cellular microvesicles containing the c-myb or HIV si RNA.

10. The method according to claim 9, wherein the step of separating the cellular microvesicles comprises one or more of differential centrifugation, immunoadsorption and ultrafiltration.

11. A research method, comprising: transferring the THP-1 cellular microvesicles carrying a c-myb siRNA or the 293T cellular microvesicles carrying a HIV siRNA of claim 1 into receptor cells, and studying an effect of the cellular microvesicles containing the c-myb or HIV siRNA on the functions of the receptor cells after transferring the cellular microvesicles.

12. A method for treating a disease associated with c-myb gene expression or viral disease, comprising transferring the THP-1 cellular microvesicles carrying a c-myb siRNA or the 293T cellular microvesicles carrying a HIV siRNA of claim 1 into receptor cells.

13. The method according claim 12, wherein the THP-1 cellular microvesicles carrying the c-myb siRNA are transferred to the receptor cells to lower expression of c-myb genes in the receptor cells.

14. The method according to claim 12, wherein the 293T cellular microvesicles carrying the HIV siRNA are transferred to the receptor cells to inhibit HIV replication in the receptor cells.

15. A method of using the cellular microvesicles containing siRNA of claim 1 in the delivery of small interfering RNAs, the method comprising:
   designing a siRNA sequence based on various sites of the sequence of a target gene selected from the group consisting of a human c-myb gene or a HIV gene and obtaining c-myb siRNA and HIV siRNA, respectively;
   transferring the c-myb siRNA into THP-1 cells or transferring the HIV siRNA into 293T cells;
   isolating THP-1 cellular microvesicles carrying c-myb siRNA or 293T cellular microvesicles carrying HIV siRNA; and
   introducing the THP-1 cellular microvesicles carrying c-myb siRNA or 293T cellular microvesicles carrying HIV siRNA into recipient cells;
   wherein the target gene is regulated through interfering the expression of the gene targeted by the siRNA.

16. The cellular microvesicles according to claim 1, wherein the cellular microvesicles are THP-1 cellular microvesicles.

17. The cellular microvesicles according to claim 16, wherein the c-myb siRNA has a nucleic acid sequence of SEQ ID NO:1.

18. The cellular microvesicles according to claim 1, wherein the cellular microvesicles are 293T cellular microvesicles.

\* \* \* \* \*